(12) United States Patent
Destrieux et al.

(10) Patent No.: US 12,085,630 B2
(45) Date of Patent: Sep. 10, 2024

(54) QUALITY CONTROL DEVICES AND METHODS FOR MAGNETIC RESONANCE IMAGING SYSTEMS

(71) Applicants: INSTITUT NATIONAL DE LA SANTE ET DE LA RECHERCHE MEDICALE (INSERM), Paris (FR); UNIVERSITÉ DE TOURS, Tours (FR); CENTRE HOSPITALIER REGIONAL UNIVERSITAIRE DE TOURS, Tours (FR)

(72) Inventors: Christophe Destrieux, Tours (FR); Laurent Barantin, Tours (FR)

(73) Assignees: INSTITUT NATIONAL DE LA SANTE ET DE LA RECHERCHE MEDICALE (INSERM), Paris (FR); UNIVERSITE DE TOURS, Tours (FR); CENTRE HOSPITALIER REGIONAL UNIVERSITAIRE DE TOURS, Tours (FR)

(*) Notice: Subject to any disclaimer, the term of this patent is extended or adjusted under 35 U.S.C. 154(b) by 271 days.

(21) Appl. No.: 17/633,328

(22) PCT Filed: Aug. 6, 2020

(86) PCT No.: PCT/EP2020/072156
§ 371 (c)(1),
(2) Date: Feb. 7, 2022

(87) PCT Pub. No.: WO2021/023825
PCT Pub. Date: Feb. 11, 2021

(65) Prior Publication Data
US 2022/0291315 A1 Sep. 15, 2022

(30) Foreign Application Priority Data
Aug. 7, 2019 (EP) .................................. 19306008

(51) Int. Cl.
*A61B 6/00* (2024.01)
*A61B 6/58* (2024.01)
*G01R 33/48* (2006.01)
*G01R 33/58* (2006.01)

(52) U.S. Cl.
CPC .......... *G01R 33/4812* (2013.01); *A61B 6/583* (2013.01); *G01R 33/58* (2013.01)

(58) Field of Classification Search
None
See application file for complete search history.

(56) References Cited

U.S. PATENT DOCUMENTS 4,692,704 A * 9/1987 Gray ...................... G01R 33/58
324/318
4,777,442 A 11/1988 Rosenthal
(Continued)

FOREIGN PATENT DOCUMENTS

| JP | 2006 141782 A | 6/2006 |
| JP | 2011512899 A | 4/2011 |
| KR | 101 358 468 B1 | 2/2014 |

OTHER PUBLICATIONS

Kittle et al: "Technical Note: Rapid prototyping of 3D grid arrays for image guided therapy quality assurance", Medical Physics, vol. 35, No. 12, p. 5708-5712, Nov. 19, 2008.
(Continued)

*Primary Examiner* — Hoon K Song
(74) *Attorney, Agent, or Firm* — WC&F IP

(57) ABSTRACT

The invention relates to quality control devices and methods for magnetic resonance imaging (MRI) systems, more particularly for medical imaging applications. An example is stereotactic surgery where MRI images are combined with X-ray images to accurately locate a target in a subject. A test device (1), and an associated method using said test object, are used to easily detect a faulty calibration or a malfunction
(Continued)

of an MRI device. The test device includes: a hermetically sealable hollow body (20) having a substantially cylindrical shape, a support frame (22) configured to be removably inserted in the hollow body and defining a target region (V22) having a substantially cylindrical shape; and a plurality of target objects (24) made of a material visible on X-ray images and MRI images said target objects being arranged in the target region and being attached to the support frame.

18 Claims, 5 Drawing Sheets

(56) References Cited

U.S. PATENT DOCUMENTS

| | | | |
|---|---|---|---|
| 5,312,755 A | 5/1994 | Madsen | |
| 6,224,257 B1* | 5/2001 | Launay | A61B 6/583 |
| | | | 250/252.1 |
| 2005/0008126 A1* | 1/2005 | Juh | A61B 6/12 |
| | | | 250/252.1 |
| 2007/0058786 A1* | 3/2007 | Michael | A61B 6/482 |
| | | | 378/207 |
| 2010/0021029 A1* | 1/2010 | Pearlstein | A61B 6/037 |
| | | | 382/128 |
| 2013/0195239 A1* | 8/2013 | O'Hare | G01N 23/046 |
| | | | 378/207 |
| 2015/0309149 A1 | 10/2015 | Holdsworth | |
| 2018/0005401 A1 | 1/2018 | Mallozzi | |

OTHER PUBLICATIONS

Mack et al: "Quality Assurance in Stereotactic Space. Determination of the Accuracy of Aim and Dose in Single Dose Radiosurgery : Bestimmung der Genauigketi von Ort und Dosis Bei Ein-Zeit-Bestrahlungen", Strahlentherapie Und Onkologie., vol. 179, No. 11, p. 760-766, Nov. 1, 2003.

* cited by examiner

QUALITY CONTROL DEVICES AND METHODS FOR MAGNETIC RESONANCE IMAGING SYSTEMS

TECHNICAL FIELD

Aspects of the invention relate to quality control devices and methods for magnetic resonance imaging systems. The invention more generally relates to the field of magnetic resonance imaging and its applications.

BACKGROUND

Magnetic resonance imaging (MRI) techniques are widely used to acquire images of various materials, such as biological tissues in a living subject.

One of the many possible applications of MRI techniques in medical imaging is stereotactic surgery, where MRI is used alongside classical imaging techniques (such as X-ray imaging) in order to accurately locate and obtain detailed images of a target inside a subject, for example for performing brain surgery in a patient.

To obtain a common geometrical reference coordinate system between the two sets of images, a stereotactic frame must be mounted on the patient during the entire image acquisition sequence.

Improperly calibrated or malfunctioning MRI devices sometimes generate images comprising anisotropic artefacts such as local geometrical deformations. If such a malfunction remains undetected, the combined location information obtained from the stereotactic imaging method will be erroneous. This may lead to a catastrophic failure of the entire surgery operation.

There is therefore a need for testing devices and methods for assessing the reliability of MRI devices.

This is usually done by using X-ray images to control the quality of images obtained from the MRI device. However, this process is long and complicated to implement.

Therefore, there is a need for easier and faster testing devices and methods for assessing the reliability of MRI devices.

SUMMARY

According to one aspect, the invention relates to a device comprising:
  an hermetically sealable hollow body having a substantially cylindrical shape;
  a support frame configured to be removably inserted in the hollow body and defining a target region having a substantially cylindrical shape; and
  a plurality of target objects made of a material visible on X-ray images and MRI images, said target objects being arranged in the target region and being attached to the support frame,
  wherein the device is configured to be firmly attached to and received in a stereotactic frame.

An advantage of the invention is that the device is easy to produce and to use and can be easily used for quality control tests in an imaging system, especially to detect a malfunctioning MRI device.

In one or more embodiments, the invention may comprise one or more of the following features, considered alone or according to all possible technical combinations:
  the target objects have a spherical shape;
  the target objects are made of a plastic material;
  the target objects are mounted on support structures connected to the support frame;
  the target objects are slidably mounted on said support structures, the device including retention elements for selectively adjusting the position of the target objects along said support structures;
  the support structures are wires made of a radio-transparent material, such as nylon;
  the hollow body includes:
    a cylindrical body configured to receive the support frame through an end opening; and
    a lid configured to hermetically close said opening;
  the hollow body has a polygonal cross-section;
  the support frame comprises:
    a lower base having a plurality of arms radially spreading from the center of the base;
    an upper base having a plurality of arms radially spreading from the principal axis; and
    at least one connection portion connecting the lower base to the upper base;
  the hollow body and the support frame are made of a non-ferromagnetic material, preferentially plastic, or wood, or glass;
  the hollow body is filled with a radio-transparent filler material, such as a fluid or a gel;
  the target objects are made of a radio opaque material;
  the filler material includes water or an aqueous solution, such as a mixture of water and an antibacterial solution;
  the device comprises between two and 50 target objects.

According to another aspect, a system comprises a device as described previously and a stereotactic frame, wherein the device is firmly attached to and received in a stereotactic frame, for example by being held inside the stereotactic frame by at least one fastening device.

According to another aspect, the invention also relates to a method for calibrating a magnetic resonance imaging apparatus including at least the following steps:
  a) acquiring a device comprising:
    an hermetically sealable hollow body having a substantially cylindrical shape;
    a support frame configured to be removably inserted in the hollow body and defining a target region having a substantially cylindrical shape; and
    a plurality of target objects made of a material visible on X-ray images and MRI images, said target objects being arranged in the target region and being attached to the support frame;
  wherein the device is firmly attached to and received in a stereotactic frame.
  b) acquiring a first image and a second image of the device using respectively a magnetic resonance imaging device and an X-ray imaging device;
  c) identifying the location of the target objects on the first and the second images,
  d) identifying pairs of corresponding target objects on the first and the second images;
  e) comparing the identified positions of the pairs of target objects;
  f) determining a fault condition of the magnetic resonance imaging device if, for at least one of the identified target objects, the position difference between a pair of target objects exceeds a predefined threshold.

BRIEF DESCRIPTION OF THE DRAWINGS

The invention will be better understood and other advantages thereof will appear more clearly upon reading the following description of exemplary quality control devices and methods for magnetic resonance imaging systems, provided solely as an example and made in reference to the appended drawings, in which.

DETAILED DESCRIPTION OF SOME EMBODIMENTS

Figure 1:
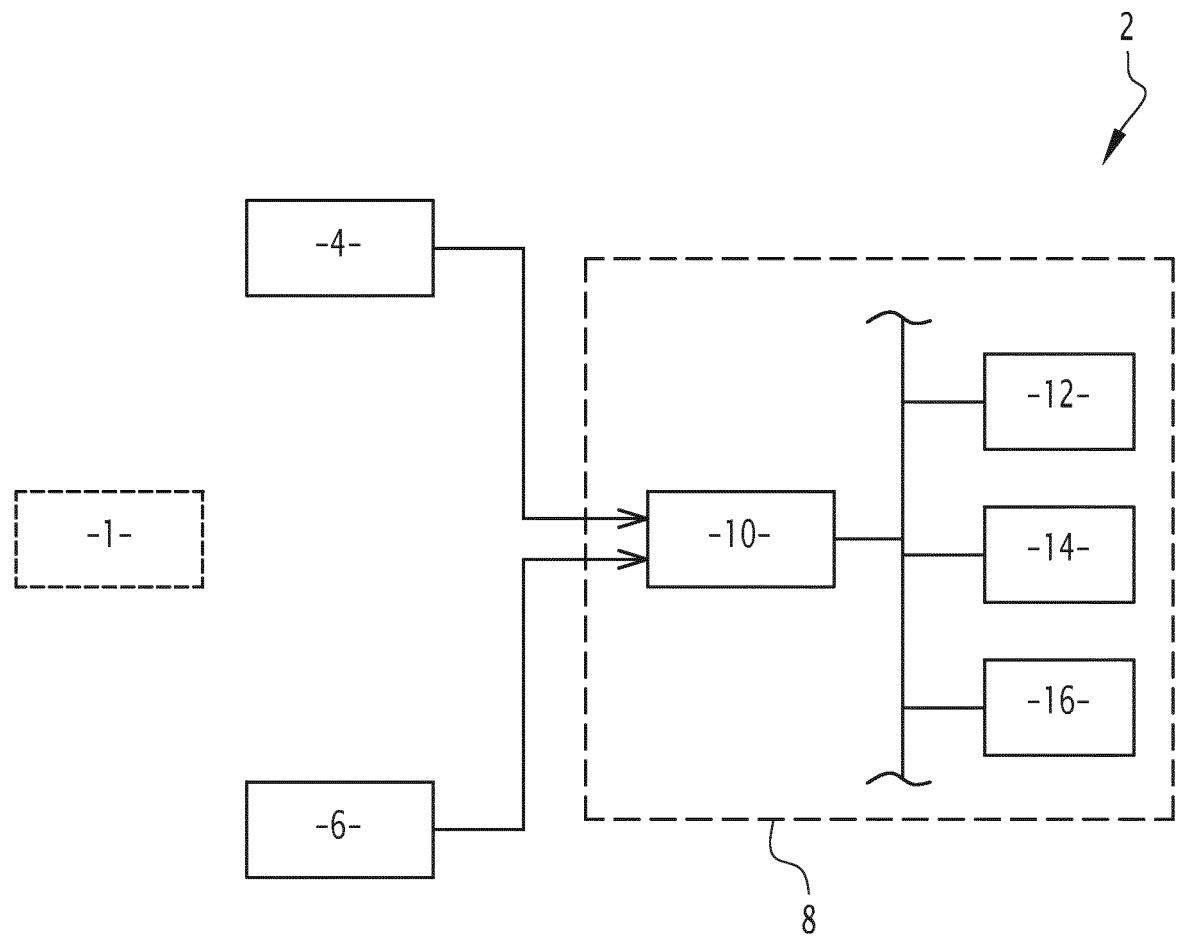
FIG. 1 is a simplified diagram of an imaging system according to some embodiments of the invention including a magnetic resonance imaging device and a X-ray device.

On FIG. 1 there is illustrated an exemplary imaging system 2 including a magnetic resonance imaging (MRI) device 4, an X-ray imaging device 6 and an electronic control system 8 for acquiring images from imaging devices 4 and 6.

According to some examples, the imaging system 2 is a medical imaging system for imaging at least one target in a subject, such as a human patient or an animal subject.

The target may correspond to an anatomical region of the subject and may include a biological tissue and/or at least one biological organ.

In the illustrated example, the imaging system 2 is configured to be used for stereotactic surgery, for example to acquire images of a subject in order to locate a target, such as an organ, in said subject during pre-operation stages.

However, it is to be understood that the invention is not limited to this exemplary application.

For example, in one or more alternative embodiments, the system 2 may be used for acquiring images to perform different types of surgery, or even for other medical imaging applications. The system 2 may also be used for imaging applications outside of the medical field, for example for performing non-destructive testing of materials.

According to some embodiments, the MRI device 4 and the X-ray device 6 are conventional imaging devices and so their structure and operation are not described in further details herein.

On FIG. 1 there is also illustrated a testing device 1 for performing quality control operations on the imaging system 1 and, more specifically, on the MRI device 4.

Embodiments of said testing device 1 are described in detail thereafter.

The electronic control system 8 is operatively coupled to the MRI device 4 and the X-ray device 6 and includes electronic circuitry programmed to acquire images of a target region of the subject from said MRI device 4 and said X-ray device 6.

In practice, the electronic control system 8 may be directly connected to the devices 4 and 6 for driving said devices, or may be connected to the respective control units of the MRI device 4 and of the X-ray device 6.

For example, the acquired images are digital images, such as DICOM images.

According to some embodiments, the electronic control system 8 includes a data acquisition interface 10, a processor (CPU) 12, a memory 14 and a user interface 16.

The processor 12 may be a programmable microcontroller, or a microprocessor, or any similar device.

The memory 14 may include a read-only memory (ROM), and/or a random access memory (RAM), and/or a non-volatile memory such as a Flash memory or a magnetic memory, or a phase change memory, or any similar memory technology.

Figure 5:
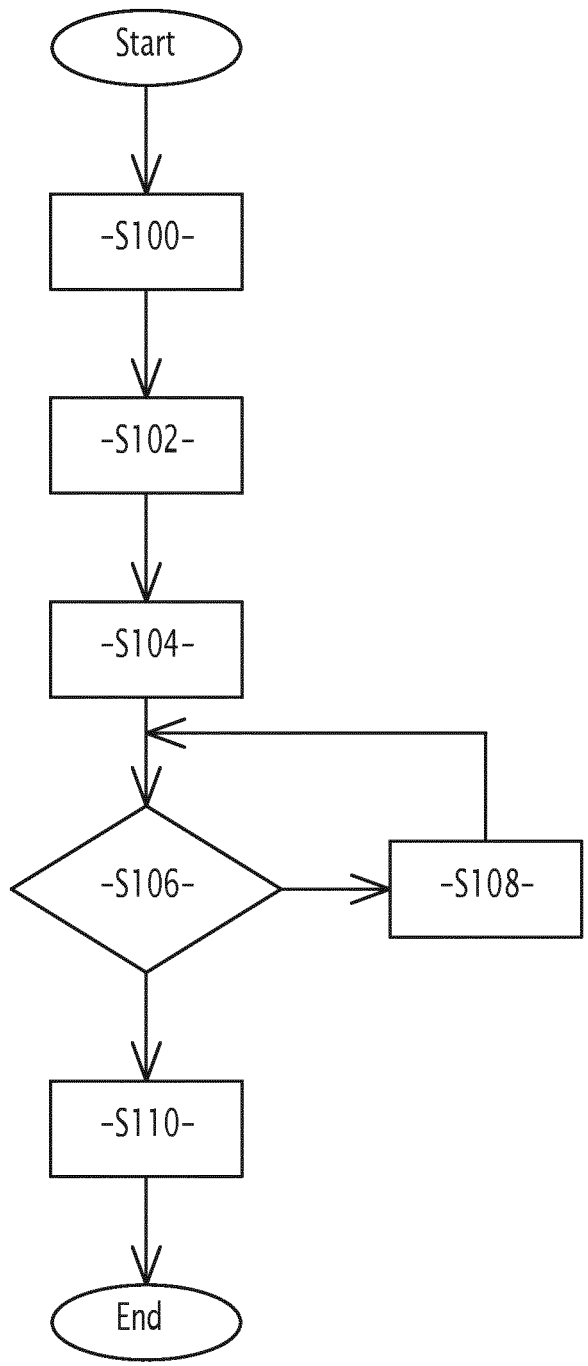
FIG. 5 is a flow chart of a quality control method according to some embodiments of the invention to assess the reliability of a magnetic resonance imaging device with regards to the positioning of target elements in a stereotactic frame.

In one or more embodiments, the memory 14 is a non-transitory computer-readable storage medium storing a computer program and/or executable machine instructions able to be executed by the processor 12 during operation of the control system 8, for example for automatically implementing at least some steps of a method according to the embodiments described in reference to FIG. 5.

In some other embodiments, the electronic control system 8 is not necessarily a processor-based device and may instead include application specific integrated circuits and/or programmable logic circuits such as field-programmable gate array circuits, or any suitable control circuitry.

Figure 2:
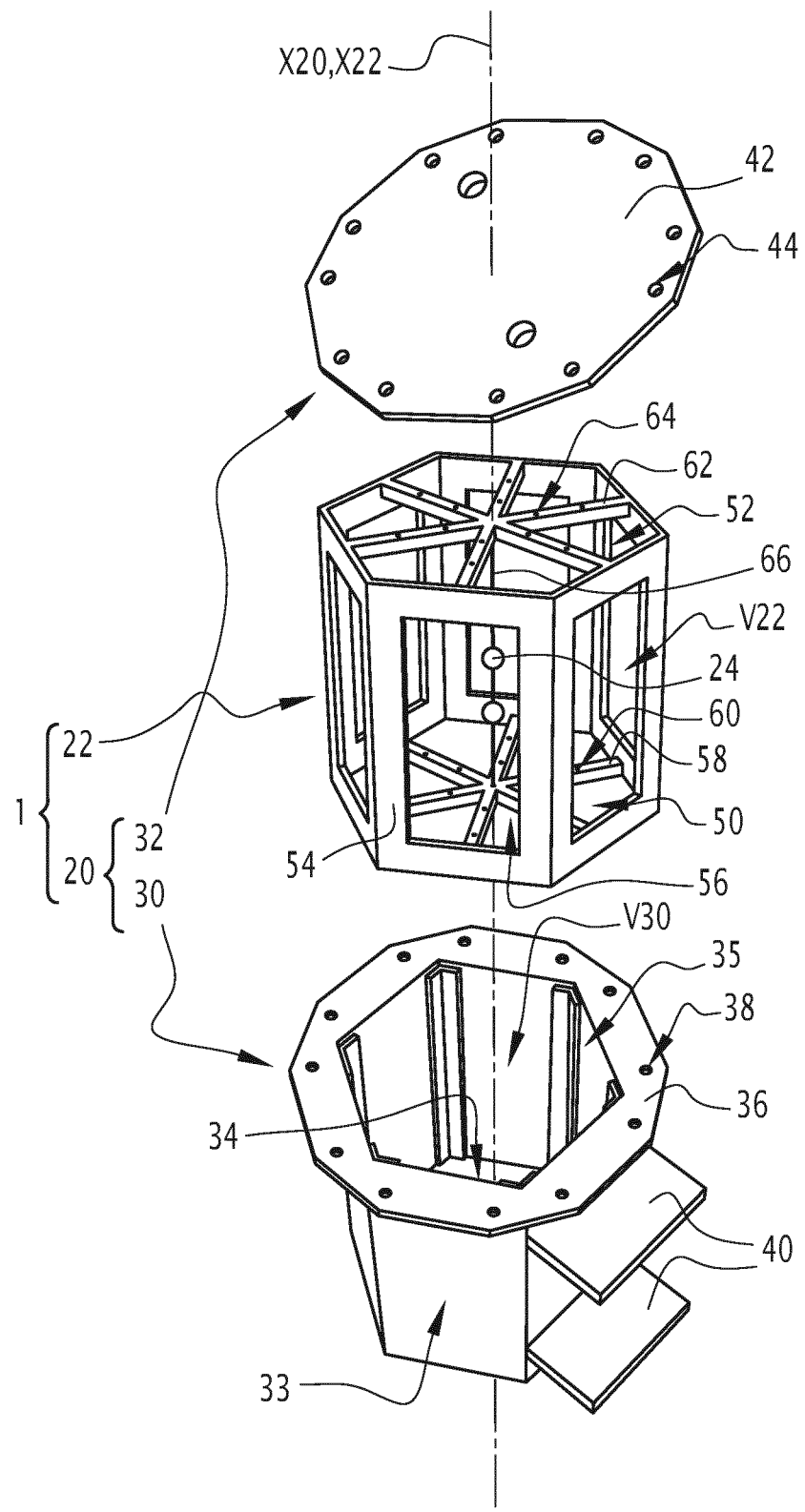
FIG. 2 is an exploded simplified view of a test device for testing the magnetic resonance imaging device of the system of FIG. 1.
Figure 3:
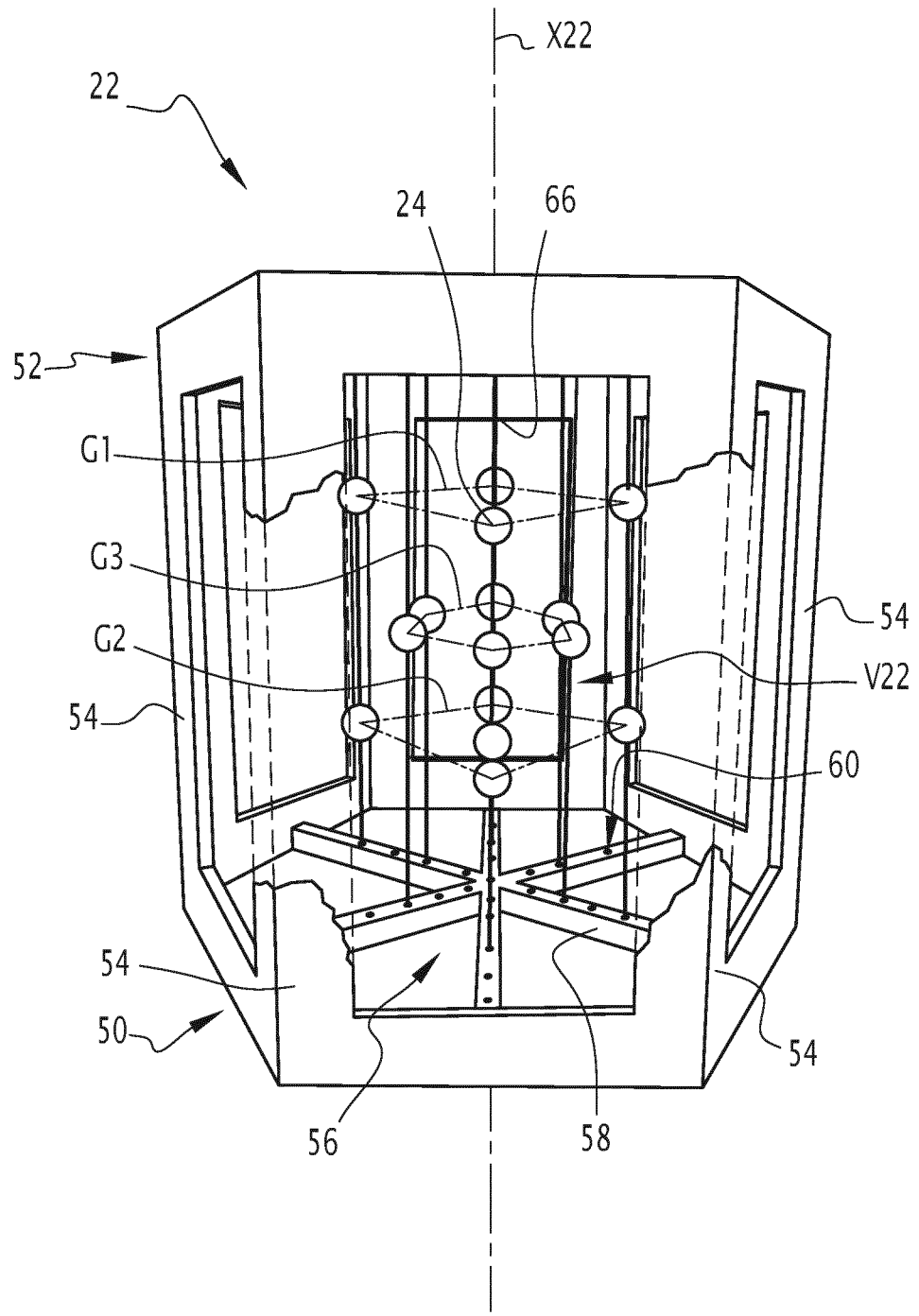
FIG. 3 is a perspective simplified view of a portion of the device of FIG. 2.
Figure 4:
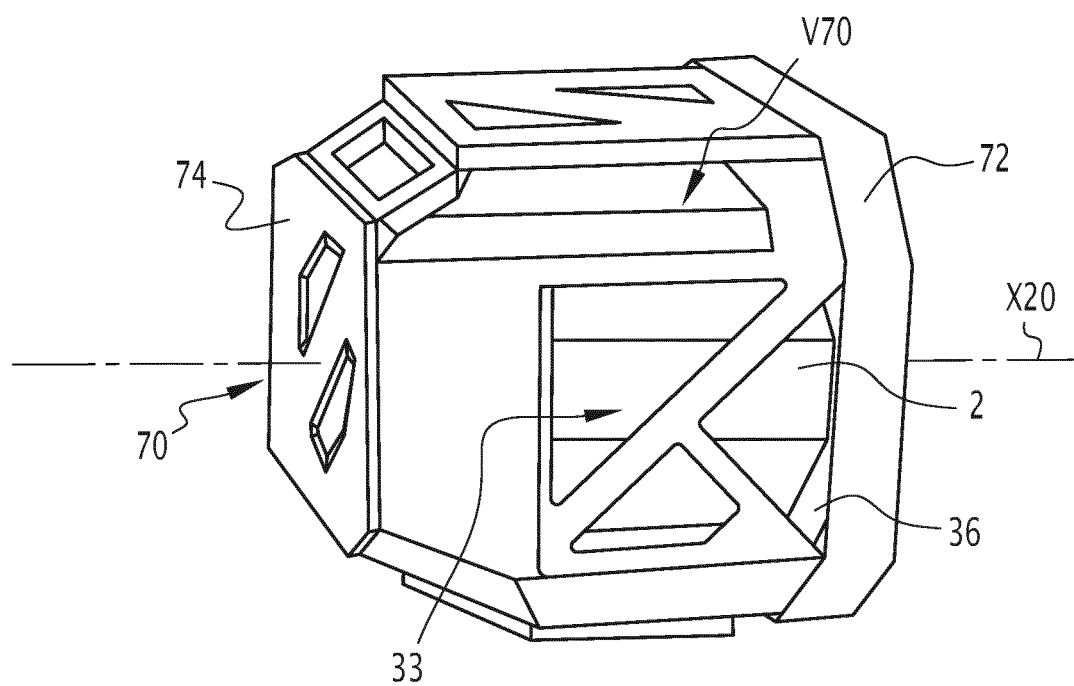
FIG. 4 is a perspective view of the test device of FIG. 2 and FIG. 3 mounted in a stereotactic Leksell frame.

Embodiments of the test device 1 are now described in greater detail in reference to FIGS. 2, 3 and 4.

As visible in FIG. 2, the test device 1 includes a hermetically sealable hollow body 20 having a substantially cylindrical shape, a support frame 22 configured to be removably inserted in the hollow body.

The support frame 22 defines a target region V22 having a substantially cylindrical shape, and a plurality of target objects 24 made of a radio opaque and MRI visible material, said target objects 24 being arranged in the target region V22 and being attached to the support frame 22.

As will be understood from the following description, said material is chosen so as to be visible on both X-ray images and MRI images. More specifically, for magnetic resonance imaging purposes, the choice of said material may also depend on properties the surrounding medium, for example so that said material may appear on MRI images by contrast to the surrounding medium.

For example, the test device 1 is configured to be used as an imaging target by the system 2 in order to detect a malfunction of the MRI device 4.

The hollow body 20 preferably includes a cylindrical body 30 or tank and a lid 32 configured to close the body 30.

In the example of FIG. 2, the body 30, the support frame 22 and the lid 32 are drawn in an exploded view to facilitate understanding of the invention.

In the illustrated example, X20 denotes a longitudinal axis of the hollow body 20 and X22 denotes a longitudinal axis of the support frame 22. When the device 1 is in an assembled configuration, axes X20 and X22 are aligned with each other.

The cross sections of the body 20 and of the frame 22 referred to thereafter are perpendicular to axes X20 and X22, respectively.

For explanatory purposes, the axes X20 and X22 are oriented vertically in the examples described and illustrated herein. In the following description, the orientation of some elements may be described as vertical or horizontal for convenience and simplicity, yet one understands that these orientations are not limiting and that the device 1 may be oriented differently, i.e. with axes X20 and X22 oriented in a non-vertical position.

The hollow body 20 and the support frame 22 are made of a non-ferromagnetic material in order to avoid interfering with the MRI device 4. For example, the body 20 and the support frame 22 are made of plastic, or wood, or glass, or any suitable material.

The hollow body 20 and the support frame 22 may be made from different materials.

In some embodiments, the hollow body 20 and/or the support frame 22 are manufactured by molding, or by additive manufacturing such as 3D-printing.

According to some exemplary embodiments, the body 30 has a substantially cylindrical shape with a polygonal cross-section, such as a hexagonal cross-section.

For example, the cylindrical body 30 includes vertically oriented side walls 33 which define an inner volume V30 closed by a closed lower end 34 and open by an upper end 35 through which the support structure 22 can be inserted and removed.

Preferably, the body 30 is shaped so as to have a cross-section similar to that of the support frame 22. In the illustrated example, the body 30 has a polygonal cross-section such as a regular polygon, for example an octagon. In this case, the side walls 33 have a flat shape.

For example, the cylindrical body 30 has a capacity of one liter of any fluid, as, for example, water or aqueous solutions. In practice, the cylindrical body 30 can contain the volume of an average human head Optionally, the body 30 may include vertical guide rails arranged inside the inner volume V30 to facilitate the insertion of the support frame 22. The guide rails are visible on FIG. 2 but are not referenced. For example, guide rails are arranged at edges between two adjacent walls 33.

In some preferred embodiments, the body 30 includes a peripheral flange portion 36 extending around the upper opening 35 and protruding radially from the upper edge of the walls 33 towards the exterior of the body 30.

The flange portion 36 includes through holes 38 adapted to receive fastening elements, such as screws or bolts or rivets, for closing the lid 32 on the top of the cylindrical body 30.

In one or more alternative embodiments, the fastening elements may be clips. In such a case, the flange portion 36 does not necessarily includes holes 38.

In other embodiments, the lid 32 is configured to be screwed onto the cylindrical body 30.

Optionally, the body 30 may include supports legs 40 that extend radially from one or several of the walls 33 towards the exterior of the body 30, thus allowing the body 30 to rest on a flat surface in an horizontal position, for example during loading or similar handling or maintenance operations. For example, the support legs 40 are placed at two or more intermediate positions along one of the walls 33.

According to some embodiments, the lid 32 has a flat shape and includes an upper face 42 and a lower face configured to be in contact with the flange portion 36.

The lid 32 is preferably made of a material similar to the material used for the remainder of the body 30.

In some embodiments, the lid 32 includes a plurality of holes 44 configured to receive fastening elements such as screws or bolts or rivets. The holes 44 are preferably arranged at the periphery of the lid 32 according to a predefined pattern so as to be aligned with the holes 38 of the flange portion 36.

The lid 32 may also include a sealing device arranged on its lower face, such as a sealing gasket, for example made from an elastomeric material.

To hermetically close the body 20, the lid 32 is positioned against the flange portion 36 so that the holes 44 are aligned with the holes 38 and then the lid 32 is pushed and held against the flange portion 36 by the fastening elements.

In many embodiments, the volume V30 is filled with a radio transparent medium, such as a liquid or a gel.

For example, a medium or material is said herein to be radio-transparent if it is invisible on X-ray images. For example, a radio transparent material has a transmission coefficient for X rays higher than 75% or than 80% or higher.

Preferably, the filler material is visible on MRI images.

According to some embodiments, the filler radio transparent medium is a phantom gel, or water, or an aqueous solution such as a mix of water with an antibacterial product.

Using water or an aqueous solution has the advantage of having MRI-related properties (such as relaxation time of atomic nuclei) similar to that of biological organs or tissues such as brain tissue. As a result, the filler medium appears on MRI images with an aspect (such a similar intensity level) similar to that of biological tissues.

The frame 22 is configured to be removably inserted in the body 30.

For example, insertion and removal of the support frame 22 is done by translating the frame 22 along the direction defined by the X20 axis.

In many embodiments, as most particularly visible in FIGS. 2 and 3, the frame 22 comprises a lower base 50, an upper base 52 and a plurality of connection portions 54, such as beams or walls, to connect the lower base 50 to the upper base 52.

For example, the connection portions 54 extend longitudinally in parallel to axis X22.

In the illustrated example, the support frame includes six connection portions 54 having a flat and rectangular shape and each including a rectangular central opening 56.

This example is not limiting and other configurations can be used as an alternative.

For example, the opening 56 may have a polygonal shape, such as a triangle, or can have a circular shape.

In some other embodiments, the number of connection portions 54 can be different. For example, the support frame 54 may include eight connection portions 54, or more, or less, depending on the actual cross-sectional shape of the support frame 22.

When the device 1 is in an assembled configuration, the support frame 22 lies inside the volume V30 with each connection portion 54 being parallel to one of the walls 33. The lower base 50 is in contact with the wall 34 and the upper base 52 lies below the flange portion 36, so that the support frame 22 is entirely included inside the volume V30 of the cylindrical body 30.

Together, the connection portions 54, the lower base 50 and the upper base 52 define the target region V22 with a substantially cylindrical shape.

For example, the region V22 has a polygonal cross-section, such a hexagonal cross-section, with similar proportions and dimensions as the cross section of the volume V30.

In some other embodiments, the cross section of the target region V22 may nonetheless differ from the cross sectional shape of the volume V30, for example by not having the same number of sides as the cross section of the volume V30.

For example, if the cross section of the volume V30 has six sides, then the cross section of the target region V22 may have eight sides and yet the cross-section of the target region V22 may still be inserted in the cross section of the volume V30.

In some other embodiments, the frame 22 may have a circular cross section.

Preferably, the volume and/or the shape of the volume V22 are chosen to be similar or identical to the volume of an anatomical region of interest of a patient. For example, the device 1 is used to test the imaging system 2 before beginning pre operatory operations ahead of a surgery on a patient.

In most embodiments, the lower base 50 includes several arms 58, for example six arms, spreading radially from the axis X22 towards the lower edge of the connection portions 54.

In the illustrated example, the distal end of each arm 58 is connected at the middle of the lower edge of a connection portion 54.

Preferably, each arm 58 is connected with only one connection portion 54.

In general, the number of arms 58 is the same as the number of connection portions 54.

According to some embodiments, each arm 58 includes a plurality of holes 60 arranged longitudinally parallel to axis X22.

Similarly, the upper base 52 includes a plurality of arms 62, for example six arms.

For example, arms 62 are spreading radially from the axis X22, each arm 62 being in connection with one connection portion 54, each connection portion 54, being in connection with only one arm 62.

According to some embodiments, each arm 62 includes a plurality of holes 64. The holes 64 are similar to the holes 60 and are aligned with the holes 60.

The target objects 24 are located inside the target region V22 and are made of a radio-opaque material, so as to be visible on X-ray images acquired using the X-ray apparatus 4.

For example, a material is said to be radio opaque if its transmission coefficient for X rays is lower than 25% or than 20% or lower.

Preferably, the target objects 24 are also made from a dense material, so as to be visible on the MRI images acquired from the MRI device 4 by contrast with the filler medium used for filling the body 30. Preferably, said material is denser than the filler medium.

In practice, the visibility of a given material on a MRI image is determined by the relaxation time of atomic nuclei inside said material. The material used for the target objects 24 is preferably chosen to exhibit a markedly different relaxation time than that of the surrounding materials (such as the filler medium in the body 30) in order to obtain a strong contrast between the target objects 24 and the surrounding medium on the acquired images.

In some embodiments, the target objects 24 are made of a plastic material, such as a thermoset polymer or any suitable material. For example, said target objects 24 are made of polyethylene terephthalate (PET), or polyethylene (PE), or polypropylene (PP), or polyvinyl chloride (PVC), or polyamide (PA), or any suitable plastic material or combination thereof.

Plastic materials provide a suitable contrast when water or any aqueous solution is used as a filler medium for filling the body 30, since water has different relaxation times than plastics.

For example, plastic material is associated to low intensity zones on the on the acquired MRI images and the filler medium is associated to high intensity zones on said acquired images. As a result, target objects 24 can be detected on MRI images by contrast with their surroundings.

In many embodiments, the target objects 24 have spherical shape, although other shapes can be chosen for alternative embodiments, such as beads or cubes.

Using a spherical shape is advantageous, as the test objects 24 are then easier to identify on digital images and their geometrical center can be easily located on such images regardless of the viewing angle, for the target objects 24 will appear as disc shaped elements regardless of the viewing angle.

For example, the diameter of the test objects 24 is comprised between 4 mm and 15 mm, and preferentially is lower than 10 mm. In an example given for illustrative purposes, test objects 24 have a diameter equal to 8 mm.

The target objects 24 are preferably made from a single piece and using a single material.

In many embodiments, each target object 24 is held in a fixed position relative to the frame 22 using support structures 66 attached to the frame 22.

On FIG. 2, only two exemplary target objects 24 are made visible for explanatory purposes. However, an embodiment including several target objects 24 is illustrated on FIG. 3, where the connection portions 54 are partially hidden to show the spatial arrangement of the target objects 24.

In the illustrated embodiments, the support structures 66 are connected to the arms 58, 62 of the respective lower and upper portions 50, 52. In many embodiments, each support structure 66 extends vertically (that is, parallel to axis X22) between the lower and upper portions 50, 52. Each wire 66 extends vertically between the lower and upper portions 50 and 52. The end of each wire 66 is inserted through a corresponding hole 60 or 64 of the lower and upper portions 50 and 52.

Preferably, the support structure 66 is configured so that the target objects 24 cannot move on their own and remain in a fixed position relative to the frame 22 once their position has been set, unless an operator deliberately moves them again.

In the example of the figures, the support structures 66 are wires, preferably wires made from a radio transparent material, such as nylon. Preferably, the support structures 66 are made from a material that is also invisible on MRI images, as is the case of nylon. Other suitable materials can be used in alternative embodiments.

According to some embodiments, the target objects 24 are threaded on the wires 66. For example, each target object 24 includes a central channel for receiving a wire 66 through the target object 24. Each target object 24 is retained in place by looping the wire 66 around the target object 24. Said wires 66 are tensioned between the arms 58 and 62 to tighten said loops and firmly secure the targets objects 24 along said wires 66.

In some other embodiments, each support structure 66 may include retention elements for selectively adjusting the position of the target objects 24 along said support structures 66. Said end of wire may be retained by a knot or by a stop element. In some other embodiments, a knot or a stop element may be associated to each target object 24. In other words, the target objects 24 are slidably mounted on at least one support structure 66 and can be translated vertically along said support structures 66. Each target object 24 can be purposefully moved by an operator along the support structure 66 by exerting a force on the target object 24.

In some alternative embodiments, each target object 24 may be attached to two or more support structures 66. The support structures 66 may also be built differently, for example using a rack and pinion system, or any other adequate mechanical translation system.

In the example of the FIG. 3, fourteen target objects 24 are arranged inside the region V22 with a central symmetry around the axis X22.

In a first group G1, four target objects 24 are arranged around axis X22 in a first geometrical plane orthogonal to axis X22.

In a second group G2, four target objects 24 form a rectangle in a second geometrical plane parallel to the first geometrical plane. In this example, each target object 24 of the second group is aligned with a target object 24 of the group G1 along an axis parallel to axis X22. A fifth target object 24 of the second group G2 is placed at a middle point between the four target objects 24 in the second plane.

In a third group G3, six target objects 24 are placed in a third geometrical plane parallel to both the first and second geometrical planes and that is equidistant from said first and second planes. For example, the target objects 24 of the third group G3 correspond to vertex of a regular hexagon centered on axis X22.

It is however to be understood that this example is merely given for illustrative purposes and that the target objects 24 may be arranged differently in many other embodiments. The number of target objects 24 may be different, and they are not necessarily arranged along one or more groups as defined above.

For example, the number of target objects may be comprised between two and 50.

For example, target objects 24 can be arranged along one or more geometrical planes that are parallel to each other and that form an angle inferior to 90° with the axis X22. In another example, target objects 24 may be placed in a specific sub-region of the volume V22, for example in the lower half of the region V22 or the upper half of the region V22. Target objects 24 can also be placed along preferential directions, such as vertical or horizontal or diagonal directions, or any other direction of interest.

This makes it possible to test the MRI device 4 so as to detect a localized defect in a subregion of the target volume V22.

The FIG. 4 illustrates the device 1 hermetically sealed and inserted into a stereotactic frame 70.

As is known, a stereotactic frame 70, such as a Leksell frame, is a medical device used in preparation for stereotactic surgery, such as brain surgery on a human subject.

In some other embodiments, the stereotactic frame 70 is a Fischer frame.

For example, a stereotactic frame is adapted to remain affixed on the head of a patient during X-ray imaging and MRI imaging sessions before surgery. The stereotactic frame is used to define a common geometrical reference, such as a coordinate system, between the sets of X-ray images and MRI images.

According to some embodiments, a crown shaped support structure 72 including at least one fastening device, not drawn in the figures, is configured to be mounted onto a patient's head. The stereotactic frame 70 is then attached onto the support structure 72, e.g. by clipping or by any other appropriate means. For example, the frame 70 includes lateral faces and a rear face 74 arranged opposite the support structure 72. The support structure 72 may have a different shape in some embodiments.

The stereotactic frame 70 includes an inner volume V70 designed to receive a portion of a subject including an anatomical region of interest, such as the head of a human patient. The device 1 is adapted to be received in the volume V70 of the stereotactic frame 70.

In other words, the device 1 is adapted to be used as a substitute for an anatomical region of interest of a patient, such as a patient's head, for performing imaging tests on both imaging devices 4 and 6.

In many embodiments, the device 1 is held inside the stereotactic frame 70 by at least one fastening device belonging to the structure 72, each fastening device being normally configured to hold the frame 70 onto a patient's head. In other words, the device 1 is attached to the stereotactic frame 70.

Preferably, the device 1 is firmly attached to the stereotactic frame 70, i.e. is attached to the stereotactic frame 70 without any degree of freedom.

In other words, once attached, the device 1 cannot move relative to the stereotactic frame 70. This prevents unwanted movements of the target objects 24 relative to the stereotactic frame 70. Another advantage is that the device 1 can be repeatedly attached to the stereotactic frame 70 in the same position.

For example, each fastening device can be a screw.

In some other embodiments, each fastening device can be a rivet or any other suitable fixation means.

For example, each fastening device has a free end configured to enter in direct contact with a patient's head when the frame 70 is mounted on a patient's head.

In some other embodiments, the structure 72 contains more than one fastening devices, for example three fastening devices or four fastening devices.

When the device 1 is received inside the volume V70, the fastening devices are in direct contact with at least one of the walls 33 of the body 30. In other words, the at least one fastening device of the stereotactic frame 70 is configured to cooperate in with at least one of the walls 33 of the body 30 of the device 1.

One of the advantages of choosing flat walls 33 and a body 30 having a polygonal cross section is that the ends of the fastening devices can easily grip the flat surfaces of the walls 33. The device 1 is therefore firmly secured inside the frame 70, which would not be the case if the body 30 had a circular cross section.

Additionally, the frame 70 may include further locking elements to hinder the translation of the device 1 along the axis X20. Said elements may include the rear face 74 or additional plates mounted on the frame 70 after insertion of the device 1.

Advantageously, the legs 40 may be configured to cooperate with the stereotactic frame 70 to hold the device 1 in place and prevent any unwanted movement of the device 1 relative to the frame 70. In some embodiments, the stereotactic frame 70 may include position markers hidden behind each face of the stereotactic frame 70. Those position markers are not visible on FIG. 4. For example, said position markers include a radiocontrast agent and a MRI contrast agent so as to be visible on both X-Ray and MRI images, such as a mixture of iodine and gadolinium. As the position markers are visible on both X-ray and MRI images, they can be used to define a common reference coordinate system for both images.

An exemplary method of using the device 1 for assessing the imaging quality of the imaging system 2 is now described in reference to the flow chart of FIG. 5.

Initially, a test device 1 according to one of the previously disclosed embodiments is acquired. Target objects 24 are moved and blocked into desired positions by an operator. Then, the frame 22 is inserted into the body 30 and the volume V30 is filled with the radio transparent material. The device 1 is inserted into the volume V70 of the frame 70 and the fastening devices are activated to block the device 1 and prevent it from moving out of the frame 70. In other words, the device 1 is attached to the stereotactic frame 70.

In a first step S100, first and second sets of images of the device 1 are acquired, using the imaging devices 4 and 6 of the system 2.

For example, the frame 70 including the device 1 is successively loaded in the MRI device 4 and in the X-ray device 6 for acquiring a set of images of the device 1 (and more specifically for acquiring images of the volume V22 including the test objects 24) with each imaging device 4 and 6.

Each set of images includes one or more images, such as digital images.

During the entire imaging sequence, the test objects 24 keep the same position relative to the frame 22. The frame 22 remains fixed relative to the body 30. The device 1 stays inside the frame 70.

In other words, the test objects 24 have theoretically the same position on both sets of images (MRI and X-ray images). If at least one test object 24 is found to have a different position between the two images, then this discrepancy can be can be attributed to a malfunction of the MRI device 4.

The images are then acquired by the electronic control system 8. As explained previously, the imaging devices 4 and 6 can be directly controlled by the electronic control system 8 or, in other embodiments, the control system 8 can automatically retrieve or be provided with the sets of digital images produced by each imaging device 4 and 6.

If each set includes more than one image, for example if the device 1 has been rotated or moved during imaging and several images have been purposefully acquired during that time to image the device under different angles, then, in some embodiments, the method may further include a step of pairing the images from each set of images.

For example, each image from the MRI image set is paired with a corresponding X-ray image for which the device 1 is in a corresponding position or orientation. This pairing can be automated and can rely on orientation data or metadata provided by the imaging devices and/or on a reference coordinate system defined in relation to the stereotactic frame 70. Any MRI or X-ray image for which no corresponding image is identified may be discarded.

During a step S102, the target objects 24 are automatically identified in each image by the control system 8 and their location is automatically identified, for example in the acquired reference coordinate system.

For example, the shape of the target objects 24 is automatically identified using a pattern recognition algorithm, such as a contour detection method, or a deep learning system. In the case of spherical target objects 24, the system is programmed to identify disc shaped objects in the images.

One understands that due to the choice of materials used for the target objects 24, the frame 22 and body 30, the frame 70 and the support structures 66, the target objects 24 are visible on the acquired images while most, if not all, of the device 1 is not visible.

The position of the target objects 24 on each image is then identified, for example by automatically determining the center of the identified shape associated to each spherical target 24. In the case of spherical target objects 24, the system is programmed to identify the center of the disc shaped identified shapes.

For example, each identified target object 24 may be automatically labeled with an unique identifier.

Then, during a step S104, pairs of corresponding target objects 24 are identified on the two images.

In some embodiments, each of the identified target objects 24 on the first image is paired with one corresponding target object 24 of the second image and, reciprocally, each of the target objects 24 of the second image is paired with one target object 24 of the first image.

For example, target objects 24 are paired together if they have a similar location, although other pairing methods or requirements may be used instead.

During a subsequent step S106, once the pairs of corresponding target objects 24 have been identified, the coordinates of the target objects 24 of each pair are compared to detect if the two objects have the same position on the respective images or if there is a position discrepancy between the two images.

For example, the comparison between the position of two target objects 24 of one pair is done by calculating the Euclidian distance between the coordinates of the two target objects 24.

To that end, a distance threshold may be defined and stored in memory.

For example, the spatial coordinates of each target object 24 identified in the first image are automatically compared with the coordinates of the corresponding target object 24 identified in the second image.

If the difference remains below the threshold, then the target object 24 is deemed to be in a correct position (step S108). The next pair of target objects 24 is selected and steps S104 and S106 is are repeated for all remaining pairs of target objects 24.

If all pairs of target objects 24 of the images are compared without identifying at least one target object 24 for which the distance exceeds the threshold, then no fault is identified for the pair of images. If there are no more pairs of acquired images to process, the method may terminate. Otherwise, the steps S104 and S106 are repeated for each pair of acquired images.

However, if for at least one pair (or a predefined number of pairs) the difference between the positions of two corresponding target objects 24 exceeds the predefined threshold, then a fault condition is identified during a subsequent step S110.

For example, a message is sent and/or displayed to an operator or to a remote computer server using the interface 16.

In some embodiments, during a subsequent step, a graphical summary is displayed on a screen for analysis by an operator.

For example, a composite image is displayed, in which the target objects 24 are colored depending on the calculated distance. The target objects 24 may be colored with a first color (e.g., green) if the calculated distance is lower than a predefined threshold, indicating a normal situation, or with a second color (e.g., red) if the calculated distance is higher than said threshold, indicating an abnormal situation.

In some embodiments, the results may be displayed as a list including spatial coordinates of the target objects 24 of each pair and the corresponding calculated Euclidian distance separating the two target objects of each pair.

Once the malfunction is identified, the surgery can be called off and maintenance of the MRI device 4 can be requested.

Thus, a method for detecting a malfunction or a faulty calibration of the MRI device 4 can be implemented using a simple test device 1. The method can be implemented easily without having to rely on complicated surgical planning software.

The embodiments and alternatives described above may be combined with each other in order to generate new embodiments of the invention.

The invention claimed is:

1. A device comprising:
   an hermetically sealable hollow body having a substantially cylindrical shape;
   a support frame configured to be removably inserted in the hollow body and defining a target region having a substantially cylindrical shape; and
   a plurality of target objects made of a material visible on X-ray images and MRI images, said target objects being arranged in the target region and being attached to the support frame,
   the device being configured to be firmly attached to and received in a stereotactic frame,
   wherein the target objects are slidably mounted on said support structures connected to support frame, the device including retention elements for selectively adjusting the position of the target objects along said support structures,
   and/or
   wherein the device is configured to be firmly attached to and received in a stereotactic frame, wherein the support frame comprises:
     a lower base having a plurality of arms radially spreading from the center of the base;
     an upper base having a plurality of arms radially spreading from the principal axis; and
     at least one connection portion connecting the lower base to the upper base.

2. The device of claim 1, wherein the target objects have a spherical shape.

3. The device of claim 1, wherein the target objects are made of a plastic material.

4. The device of claim 1, wherein the support structures are wires made of a radio-transparent material.

5. The device of claim 1, wherein the hollow body includes:
   a cylindrical body configured to receive the support frame through an end opening; and
   a lid configured to hermetically close said opening.

6. The device of claim 1, wherein the hollow body has a polygonal cross-section.

7. The device of claim 1, wherein the support frame comprises:
   a lower base having a plurality of arms radially spreading from the center of the base;
   an upper base having a plurality of arms radially spreading from the principal axis; and
   at least one connection portion connecting the lower base to the upper base.

8. The device of claim 1, wherein the hollow body and the support frame are made of a non-ferromagnetic material.

9. The device of claim 1, wherein the hollow body is filled with a radio-transparent filler material.

10. The device of claim 9, wherein the target objects are made of a radio opaque material.

11. The device of claim 9, wherein the filler material includes water or an aqueous solution.

12. A system comprising a device of claim 1 and a stereotactic frame, wherein the device is firmly attached to and received in a stereotactic frame, for example by being held inside the stereotactic frame by at least one fastening device.

13. A method comprising:
   a) acquiring a device comprising:
     an hermetically sealable hollow body having a substantially cylindrical shape;
     a support frame configured to be removably inserted in the hollow body and defining a target region having a substantially cylindrical shape; and
     a plurality of target objects made of a material visible on X-ray images and MRI images, said target objects being arranged in the target region and being attached to the support frame,
     wherein the device is firmly attached to and received in a stereotactic frame;
   b) acquiring a first image and a second image of the device using respectively a magnetic resonance imaging device and an X-ray imaging device;
   c) identifying the location of the target objects on the first and the second images,
   d) identifying pairs of corresponding target objects on the first and the second images;
   e) comparing the identified positions of the pairs of target objects; and
   f) determining a fault condition of the magnetic resonance imaging device if, for at least one of the identified target objects, the position difference between a pair of target objects exceeds a predefined threshold.

14. The device of claim 4, wherein the radio-transparent material is nylon.

15. The device of claim 8, wherein the non-ferromagnetic material is plastic, or wood, or glass.

16. The device of claim 9, wherein the radio-transparent filler material is a fluid or a gel.

17. The method of claim 11, wherein the filler material includes a mixture of water and an antibacterial solution.

18. The system of claim 12, wherein the device is held inside the stereotactic frame by at least one fastening device.

* * * * *